US00PP15513P3

(12) United States Plant Patent
Utecht

(10) Patent No.: US PP15,513 P3
(45) Date of Patent: Feb. 1, 2005

(54) ***GERANIUM* PLANT NAMED 'FISRODARK'**

(50) Latin Name: *Pelargonium zonale*
Varietal Denomination: Fisrodark

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 192 days.

(21) Appl. No.: 10/715,427

(22) Filed: Nov. 19, 2003

(65) Prior Publication Data

US 2004/0123362 P1 Jun. 24, 2004

(30) Foreign Application Priority Data

Dec. 23, 2002 (CA) ..... PBR 02-3406

(51) Int. Cl.[7] ..... A01H 5/00

(52) U.S. Cl. ..... Plt./330

(58) Field of Search ..... Plt./330

*Primary Examiner*—Kent Bell

(74) *Attorney, Agent, or Firm*—Foley & Lardner LLP

(57) ABSTRACT

A new and distinct cultivar of *geranium* plant named 'Fisrodark', particularly characterized by the combined features of deep red, semi-double flowers, medium spring flowering response, and floriferous throughout the summer, medium-green foliage with weak zonation, relatively large leaves, vigorous growth and tall, wide plant habit.

1 Drawing Sheet

Genus and species of the plant claimed: Hybrid *Pelargonium zonale L'Héritier.*
Variety denomination: 'Fisrodark'.

BACKGROUND OF THE INVENTION

The present invention comprises a new and distinct cultivar of *geranium*, botanically known as *Pelargonium zonale*, and hereinafter referred to by the cultivar name 'Fisrodark'.

'Fisrodark' is a product of a planned breeding program which had the objective of creating new zonal *geranium* cultivars with cultivars with semi-double flowers, relatively vigorous, but well-branched growth habit, good outdoor performance, and in various flower colors.

'Fisrodark' was originated from a hybridization made by the inventor, Angelika Utecht, in a controlled breeding program in Hillscheid, Germany, in 1998.

The female parent was the patented variety 'Americana Dark Red' (U.S. Plant Pat. No. 9,307), having deep-red semi-double flowers, medium green foliage, and vigorous growth. The male parent of 'Fisrodark' was the variety 'Fisfire' (U.S. Plant Pat. No. 12,489), and characterized by scarlet, semi-double flowers, leaves with strong zonation, and about medium sized plant habit.

'Fisrodark' was selected as one flowering plant within the progeny of the stated cross by Angelika Utecht in 1999 in a controlled environment in Moncarapacho, Portugal.

The first act of asexual reproduction of 'Fisrodark' was accomplished when vegetative cuttings were taken from the initial selection in the fall of 1999 in a controlled environment in Moncarapacho, Portugal, by, or under the supervision of, Angelika Utecht.

Horticultural examination of plants grown from cuttings of the plant initiated in May 2000 in Hillscheid, Federal Republic of Germany, and continuing thereafter, has demonstrated that the combination of characteristics as herein disclosed for 'Fisrodark' are firmly fixed and are retained through successive generations of asexual reproduction. 'Fisrodark' has not been observed under all possible environmental conditions. The phenotype may vary significantly with variations in environment such as temperature, light intensity and day length.

BRIEF SUMMARY OF THE INVENTION

The following observations, measurements, and comparisons describe plants grown in Hillscheid, Germany, under greenhouse conditions which approximate those generally used in commercial practice.

The following traits have been repeatedly observed and are determined to be basic characteristics of 'Fisrodark' in combination distinguish this *geranium* as a new and distinct cultivar:

1. Deep red, semi-double, round flowers;
2. Numerous, medium-sized to large inflorescences, thin peduncles;
3. Medium-green foliage with weak zonation;
4. Vigorous growth, tall plant and well-branched plant habit; and
5. About mid season spring flowering response.

Of the many commercial cultivars known to the present inventor, the most similar in comparison to 'Fisrodark' is the variety 'Fip 553' (U.S. Plant Pat. No. 13,961), and the parental variety 'Americana Dark Red'. In comparison to 'Fip 533', 'Fisrodark' has even deeper red flower color, without a trace of orange-red. Its flower-heads are not quite as big, peduncles are thinner, but it is more floriferous than 'Fip 553'. Additionally, leaves of 'Fisrodark' show somewhat less distinct zonation than the foliage of 'Fip 553'.

In comparison to 'Americana Dark Red', flowers of 'Fisrodark' are a true deep red, they lack the slightly bluish overtone of lower petals. Furthermore, 'Fisrodark' has somewhat deeper green foliage with stronger zonation, while leaves of 'Americana Dark Red' develop no or only very slight zonation.

BRIEF DESCRIPTION OF THE DRAWING

The accompanying photographic drawing shows typical flower and foliage characteristics of 'Fisrodark' with colors being as true as possible with an illustration of this type. The photograph drawing shows a flowering potted plant of 'Fisrodark'.

DETAILED BOTANICAL DESCRIPTION

The measurements were taken in Hillscheid, Germany, in mid May 2003, 11 weeks after planting of rooted cuttings. The plants were growing in 14 cm pots, they had not been pinched.

In the following description color references are made to The Royal Horticultural Society Color Chart. The color values were determined indoors from plants growing in a green-house in May, 2003, in Hillscheid, Germany.

INFLORESCENCE

Umbel:

*Shape.*—Umbrella-shape to semi-spherical.
*Average diameter.*—122 mm.
*Average depth.*—65 mm.
*Peduncle.*—245 mm in length, relatively thin, often only 2–3 mm in diameter.
*Peduncle color.*—Light green, RHS 143 C, outdoors a slight tinge of brown may occur, RHS 147 B.
*Pedicel.*—38 mm in length.
*Pedicel color.*—Lower part green, RHS N144A, upper part reddish-brown, RHS 181 A.
*Number of flowers per umbel.*—About 25–40.

Corolla:

*Average diameter.*—57 mm.
*Form.*—Semi-double.
*Shape.*—Round, open, cup-shape.
*Number of petals.*—7–9.
*Number of petaloids.*—Typically none.
*Shape of petals.*—Obovate, base acute or attenuate, upper end is rounded, margin is entire.
*Size of petals.*—Upper petals: 25–27 mm long, 21–23 mm wide; lower petals: 22–23 mm long, 23–24 mm wide.
*Color (general tonality from a distance of three meters).*—Brilliant deep red, uniform.
*Color of upper petals.*—Mainly RHS 45 A, near the base RHS 44 A.
*Markings of upper petals.*—No markings.
*Color of lower petals.*—RHS 45 A.
*Markings of lower petals.*—Absent.
*Color of lower surface of petals.*—RHS 43 A.
*Color of sepals.*—Outer surface: light green between RHS 144 A and 143 B, RHS 181 B at the base; inner surface: light green, RHS 143 C, base RHS 180 B.
*Number of sepals.*—5.
*Shape of sepals.*—Linear to lanceolate, acute tip, sessile, surface with very weak pubescence, margin entire.
*Size of sepals.*—10–11 mm long, 4–5 mm wide for the largest, upper sepal, 3–4 mm in width for the other sepals.

Bud: (just prior to petals unfolding):

*Shape.*—Elliptical.
*Color of sepals.*—Light green, RHS 143 C.
*Color of petals.*—RHS 45 B.
*Length.*—15 mm.
*Width.*—10 mm.

REPRODUCTIVE ORGANS

*Androecium.*—7–9 fertile anthers, plenty pollen, yellow-orange, RHS 28 A, filaments white, RHS 155 D, to light-pink, RHS 65A.
*Gynoecium.*—One pistil, reddish style, RHS 153D, stigma 5–6-lobed stigma, dark-red, RHS 46A.
*Fertility/seed set.*—Occasionally weak seed set, mainly in late summer to fall.
*Fruit.*—Oblong, about 5–6 mm wide, rostrum (beak) 37–40 mm long.
*Seed.*—Oblong, 4–5 mm long, brown, RHS 177 B.
*Spring flowering response period.*—In Hillscheid, Germany, in 2001, plants had on average 0.4 flowers opened 8 weeks after planting of rooted cuttings.
*Outdoor flower production.*—Continuously and rich flowering, the flower count in 2003 in Hillsheid, Germany, indicated about 3–3.5 inflorescence per plant in mid May.
*Durability.*—Basically good stability of flower color, however, flowers tend to being scorched by intense sun light, which is typical for this color group, good rain resistance.
*Lastingness of the individual flower.*—About 7–8 days at 18° C., about 13–15 days for the umbel.
*Fragrance.*—None.

PLANT

Foliage:

*Shape.*—Kidney-shaped, with cordate base, with the gap between the lowest lobes somewhat open, apex rounded with very weak lobes.
*Margin.*—Bi-crenate, relatively weak.
*Texture.*—Upper surface smooth.
*Size of leaf.*—117 mm wide, 71 mm long.
*Color of upper surface.*—Medium green, approximately RHS 137 C.
*Zone color.*—Weak, brown, about RHS 166 A.
*Color of lower surface.*—Between RHS 137 D and 139 C.
*Petioles.*—60–90 mm long, 3 mm diameter, light green in color, between RHS 137 D and 143 A.

General appearance and form:

*Stem color.*—Grass-green, RHS 143 B.
*Internode length.*—35–40 mm.
*Branching pattern.*—7 branches on average.
*Size of plants.*—25.6 cm tall, 39.8 cm wide, (11-week-old plants, as described, measured from the top of the soil (base of the main stem) to the surface of the foliage canopy, without inflorescences.

I claim:

1. A new and distinct cultivar of *geranium* plant named 'Fisrodark', as described and illustrated herein.

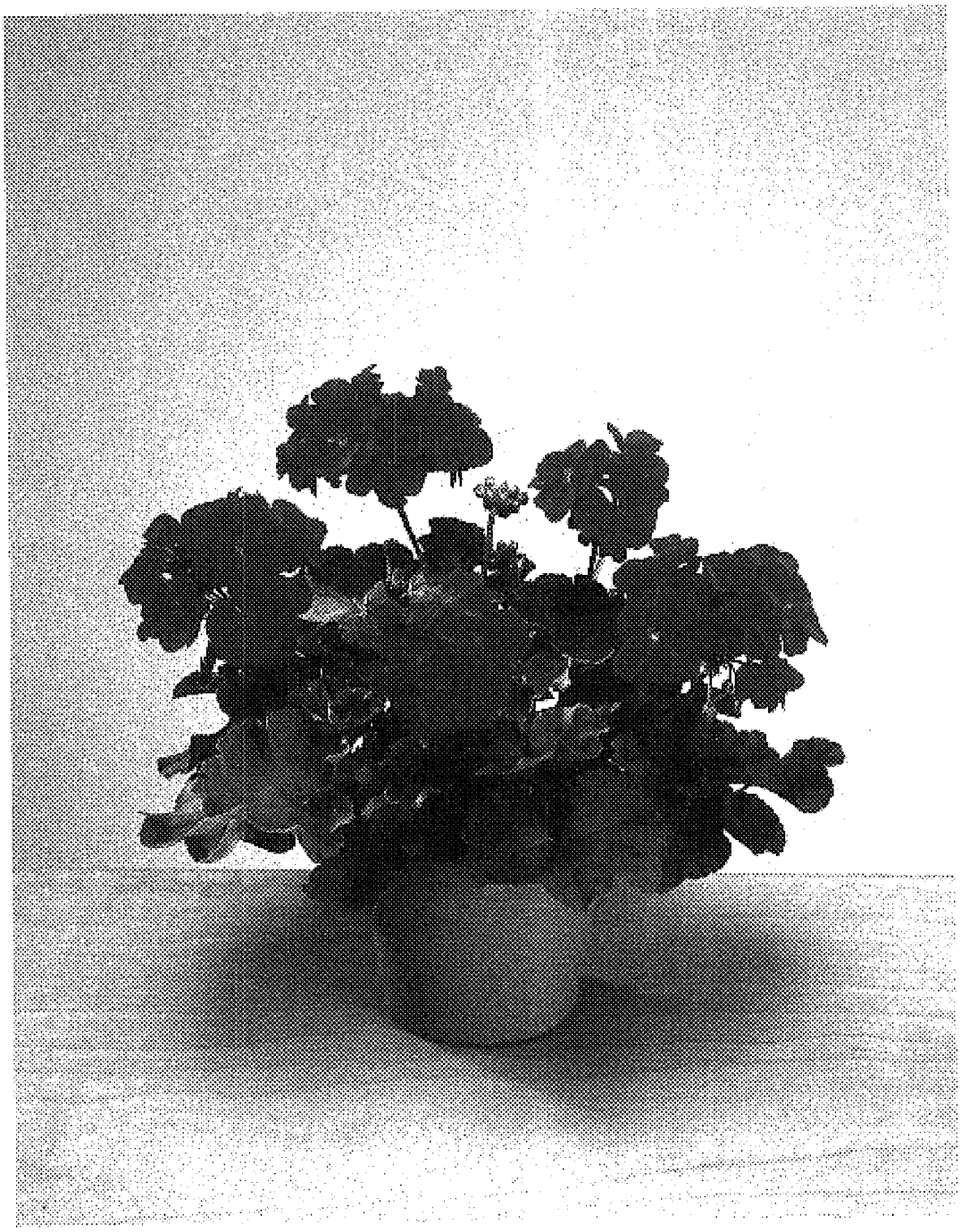

* * * * *